United States Patent [19]

Mintz

[11] Patent Number: 5,154,082

[45] Date of Patent: Oct. 13, 1992

[54] MICROPROCESSOR-CONTROLLED APPARATUS AND METHOD FOR DETECTING THE COAGULATION OF BLOOD

[75] Inventor: Michael D. Mintz, Edison, N.J.

[73] Assignee: International Technidyne Corporation, Edison, N.J.

[21] Appl. No.: 703,288

[22] Filed: May 20, 1991

[51] Int. Cl.⁵ .......................................... G01N 33/49
[52] U.S. Cl. ................................ 73/64.41; 422/73
[58] Field of Search ................. 73/64.41, 64.42, 64.43; 422/73; 436/69

[56] References Cited

U.S. PATENT DOCUMENTS 3,695,842 10/1972 Mintz ............................ 73/64.41 X
3,836,333 9/1974 Mintz ............................ 73/64.41 X

FOREIGN PATENT DOCUMENTS 2410817 6/1979 France ............................ 73/64.42

Primary Examiner—Hezron E. Williams
Assistant Examiner—Joseph W. Roskos
Attorney, Agent, or Firm—Arthur L. Plevy

[57] ABSTRACT

Apparatus and method for detecting the coagulation of a sample of blood includes a ferromagnetic member, which is immersed in the blood sample and which is magnetically coupled to a reed switch, and an adjustable source of magnetic flux lines, which is also magnetically coupled to the reed switch. As the blood sample coagulates, the ferromagnetic member is displaced from the reed switch and, as a result, the magnetic field coupled to reed switch is reduced. When the ferromagnetic member reaches a predetermined displacement, the reed switch is open, which indicates that blood has coagulated. A microprocessor calibrates the reed switch by adjusting the density of the magnetic flux lines from the adjustable source such that the reed switch is open when the ferromagnetic member reaches the predetermined distance displacement.

20 Claims, 11 Drawing Sheets

MICROPROCESSOR-CONTROLLED APPARATUS AND METHOD FOR DETECTING THE COAGULATION OF BLOOD

BACKGROUND OF THE INVENTION

The present invention relates in general to apparatus and methods for detecting the coagulation of blood, and in particular to microprocessor-controlled apparatus and method for detecting changes in a magnetic field adjacent to a zone containing a blood sample, which changes indicate that the blood has coagulated.

The formation of clots within the circulatory system has been known to result in serious, if not fatal, consequences, particularly when the clot lodges within the heart or the brain. To prevent clots from occurring, coagulation inhibiting agents are normally administered to a patient. As a prerequisite for administering the coagulation inhibiting agents, the level of inhibiting agents within the patient's circulatory system must be known. The time required for clot formation within a standard laboratory test tube has been interpreted as an indication of the level of such inhibiting agents within a patient's circulatory system.

A system and a method for automatically measuring clotting time is disclosed in U.S. Pat. No. 3,695,842 entitled "METHOD AND SYSTEM FOR ANALYZING A LIQUID", issued to Michael D. Mintz on Oct. 30, 1972 and assigned to International Technidyne Corporation, the assignee of the present invention. A sample of blood is placed in a test tube and a permanent magnet is immersed in the blood sample. A magnetic reed switch, which is normally open, is positioned directly below the magnet. Flux lines, provided by the magnet, pass through the reed switch, causing it to close. Then, a relative rotational motion is produced between the test tube and the magnet to agitate the blood, during which time the magnet remains positioned over the reed switch. When the blood coagulates, the resulting fibrous strands of clotted sample causes the magnet to move conjointly with the test tube. Thus, the magnet is displaced from the reed switch. This displacement causes a reduction in the density of the magnetic flux lines passing through the reed switch (i.e., weakens the magnetic field). As a result, the reed switch opens and a signal is generated, indicating the occurrence of the coagulation of blood.

An improved system for measuring clotting time is disclosed in U.S. Pat. No. 3,836,333 entitled "SYSTEM FOR TIMING THE COAGULATION OF BLOOD" issued to Michael D. Mintz on 30 Oct. 1972 and assigned to International Technidyne Corporation. An electromagnetic bias coil, which is wound around the reed switch, provides steady-state magnetic flux lines that supplement the flux lines provided by the permanent magnet. When the density of the flux lines passing through the reed switch decreases as a result of the magnet being displaced, the reed switch opens. The bias coil also provides a magnetic pulse, which forces the reed switch to a closed state. This system is manufactured under the trademark HEMOCHRON by International Technidyne Corporation at Edison, N.J.

The precision with which the system detects the coagulation of blood is dependant upon the ability of the reed switch to respond to changes in density of the magnetic flux lines. To ensure that the reed switch opens and closes in the presence of the correct flux densities, the reed switch must be manufactured with a great deal of precision. When tested, any reed switch that does not operate as specified must be eliminated. This results in additional expense as high precision switches are inherently more costly.

One problem encountered in using a reed switch for magnetic field measurement relates to the process of magnetic hysteresis. The effect of hysteresis in a reed switch is to require a greater magnetic flux density to initially close the reeds than that required to simply maintain the reeds in a closed condition. In the system described above, the difference between the magnetic field required to close the reeds and the magnetic field at which the reeds just reopened must be less than the difference in magnetic field passing through the reed switch when the magnet is directly above the reed switch and when the magnet has been displaced relative to the reed switch.

A second problem with reed switches relates to magnetic storage or magnetization. The reeds of the switch are made of a ferromagnetic material. During operation, when magnetic flux lines pass through the reed switch, the reeds store energy at a slow rate and, therefore, become magnetized. As a result of the stored magnetic energy, the reed switch becomes a time-dependant storage device, which may fail to open or close precisely at predetermined external flux level. Thus, a reed switch employed in the system described above may not switch states precisely when the blood clots.

Therefore, it is an object of the present invention to eliminate the need for a high-precision reed switch in a system for detecting the coagulation of blood.

It is a further object of the present invention to eliminate the effects of magnetic hysteresis and magnetic storage in the reed switch in such a system.

It is still a further object of the present invention to provide a technique for calibrating a reed switch in such a system.

SUMMARY OF THE INVENTION

The disadvantages of the prior art systems for detecting the transformation of blood from a liquid to a clot are overcome by the present invention. The present invention comprises adjustable-variable source means for providing magnetic flux lines having a density that varies in a time-repetitive sequence; switching means, magnetically coupled to the adjustable-variable source means by the flux lines, for switching from a second state to a first state when the density of the flux lines enters a first density region; determining means, responsive to the switching means, for determining the first density region of the flux lines; and adjusting means, responsive to the determining means and operative on the adjustable-variable source means, for adjusting the density of the flux lines at a first level. When the density of the flux lines is adjusted to the first level, the variation of the magnetic flux lines causes the density of the flux lines to fall outside of the first density region, whereby the coagulation of blood causes the switching means to switch from the first state to the second state or whereby the coagulation of blood causes the switching means not to switch from the second state.

The present invention further includes a method for detecting the coagulation of blood with a system including a vessel containing the blood; adjustable magnetic field means, located external the vessel, for providing an adjustable magnetic field; a ferromagnetic member, disposed within the vessel, for providing a permanent magnetic field; and a normally-open reed switch, magnetically coupled to the adjustable magnetic field means by the adjustable magnetic field. The method comprises the steps of (a) adjusting the adjustable magnetic field to a first level at which the reed closes; (b) placing the ferromagnetic member in proximity of the reed switch; (c) adjusting the adjustable magnetic field to a second level at which the reed switch opens; (d) rotating the vessel to create a relative rotational motion between the ferromagnetic member and the vessel; (e) adjusting the adjustable magnetic field to a third level; and (f) monitoring the state of the reed switch, whereupon if the blood has coagulated the reed switch remains open.

DETAILED DESCRIPTION OF THE EXEMPLARY EMBODIMENTS

Figure 1:
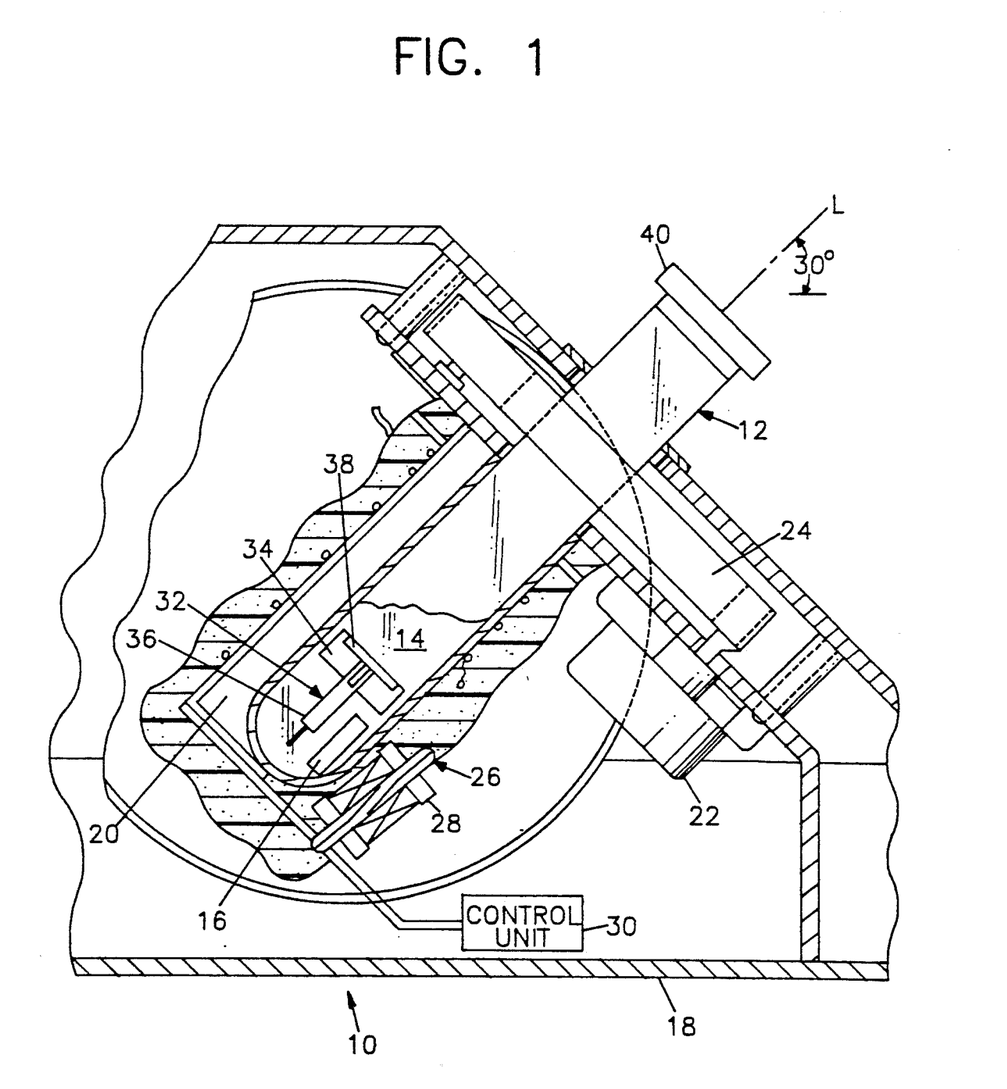
FIG. 1 is a cross-sectional view of a system for detecting the coagulation of blood in accordance with the present invention.

Referring to FIG. 1, there is shown a system 10 for detecting the coagulation of blood according to the present invention. The system lo comprises a test tube 12, which contains a sample of blood 14 to be tested, a cylindrical bar magnet 16, which is immersed in the blood 14, and an analyzer 18, which has a test well 20. The test tube 12 is inserted into the test well 20, where its longitudinal axis L is inclined at 30 degrees from horizontal. Gravity causes the magnet 16 to settle to the lowest position of the test tube 12, hereinafter referred to as the initial position. The analyzer 18 includes a drive motor 22, which is provided with a transmission 24 for rotating the test tube 12 about its longitudinal axis L. A reed switch 26, which forms a part of the analyzer 18, is located beneath the magnet 16, as close as possible to the test tube 12. Flux lines provided by the magnet 16 pass through the reed switch 26. A solenoid-wound bias coil 28 is wrapped around the reed switch 26. When the bias coil 28 is energized, it provides a second source of magnetic flux lines, which also pass through the reed switch 26.

The analytic operation of the system 10 is controlled automatically by a control unit 30. The control unit 30 commands the drive motor 22 to rotate the test tube 12 about its longitudinal axis L. While the test tube 12 is rotating, the magnet 16 is held in its initial position by its magnetic attraction to the reed switch 26 and by gravitational forces. In the unclotted condition, blood 14 behaves as a liquid (i.e., the unclotted blood 14 does not support shear forces) and, therefore, the magnet 16 does not rotate with the test tube 12. As a result, there is produced a relative motion between the test tube 12 and the magnet 16.

Immediately after commanding the drive motor 22 to rotate the test tube 12, the control unit 30 energizes the bias coil 28. The magnetic flux densities produced by magnet 16, bias coil 28, and unshielded ambient conditions (i.e., magnetic fields produced by the drive motor 22, other electromagnetic equipment and the earth's field) are added vectorially to produce the total effective magnetic flux density acting on the reed switch 26. For simplicity, however, only the flux densities of the magnet 16 and bias coil 28 shall be considered. In combination, the magnetic flux lines from the magnet 16 and bias coil 28 combine to cause the reed switch 26 to open and close in a periodic or cyclic manner.

The magnet 16 remains substantially in its initial position within the test tube 12 until the formation of a fibrous strand of clotted sample. The clotted sample functions to adhere the magnet 16 to the rotating wall of the test tube 12. When the adhesive forces of the clotted sample are sufficient to overcome the gravitational and magnetic forces, the test tube 12 pulls the magnet 16 away from its initial position. The displacement of the magnet 16 from its initial position causes a reduction in the density of the magnetic flux lines passing through the reed switch 26. Once the magnetic flux density is sufficiently reduced, the reed switch 26 fails to alternate between open and closed states, whereupon the control unit 30, which monitors the cyclic switching of the state of the reed switch 26, indicates that the blood 14 has coagulated.

Still referring to FIG. 1, the test tube 12 is a cylindrical vessel having a closed end and an open end. The test tube 12 is made of a nonferromagnetic material such as glass or plastic. The open end of the test tube 12 may be sealed by stopper 40. A blood sample 14 is injected into the test tube 12 through the open end. If the test tube is stoppered, the material of which the stopper is composed must be a soft plastic or elastomeric.

A plastic wedge 32 is located and frictionally engages the inner walls at the closed end of the test tube 12. Four rectangular shaped fins 34 extend radially from a central hub 36 and frictionally engage the walls of test tube 12. The central hub 36 is attached to a spacer disk 38, which retains the magnet 16 within the lower zone of test tube 12. The wedge 32 functions to displace the magnet 16. As the test tube 12 is rotated and the blood 14 has yet to coagulate, the magnet 16 remains relatively motionless. Once the blood 14 coagulates, however, the clot provides a mechanical "grip" which adheres one end of the magnet 16 to the wedge 32. Thus as the test tube 12 and magnet 16 begin to rotate conjointly, the magnet 16 is pulled out of alignment with the central hub 36 of the plastic wedge 32 and attains an oblique angle with respect to longitudinal axis L. As a result, the magnet 16 "toggles" wherein each end of the magnet 16 touches a different point on the test tube 12 wall, and the center of magnet 16 contacts a point in the central hub 36 of wedge 32. Then, the wedge 32 helps displace the magnet 16 upwards and away from the initial position.

Figure 2:
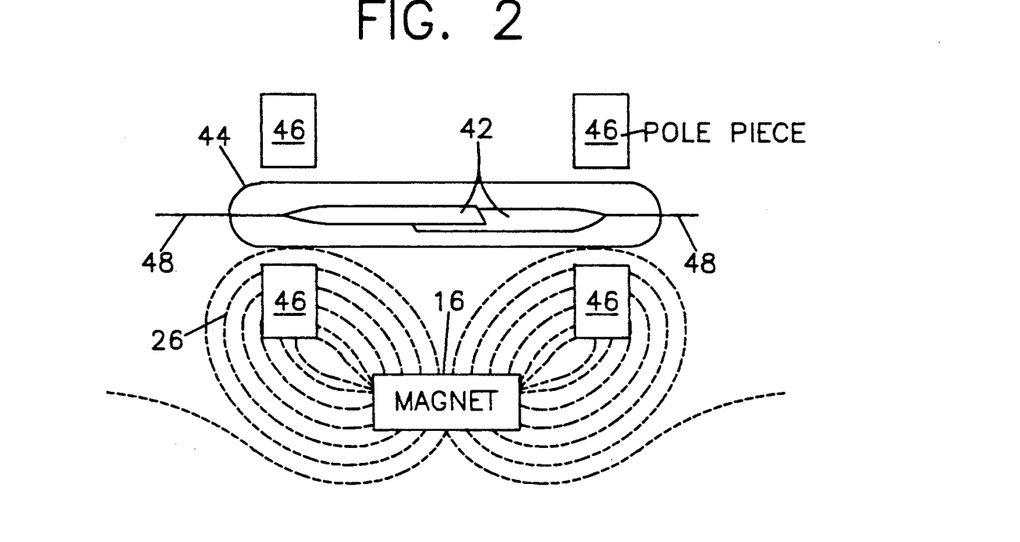
FIG. 2 is a schematic diagram of a reed switch, which forms a part of the system illustrated in FIG. 1.

Referring now to FIG. 2, there is shown a reed switch 26 according to the present invention. The reed switch 26 includes two overlapping ferromagnetic narrow strips or reeds 42 of metal contained within a glass envelope 44. The reeds 42 are separated by a gap and are positioned parallel to the magnet 16 when the magnet 16 is located at its initial position. As previously noted, the bias coil 28 is wrapped around the reed switch 26. The magnetic flux lines provided by the bias coil 28 are essentially colinear with reeds 42. Ferromagnetic pole pieces 46 attached to each end of the reed switch 26 serve to align the magnetic flux lines, thereby increasing the sensitivity of the reed switch 26 to the magnetic fields provided by the magnet 16 and the bias coil 28. The axial leads 48 of the reed switch 26 are an extension of the reeds 42 themselves, and thus, also serve to align the magnetic flux lines. Any bending or clipping of these axial leads 48 affects the operating characteristics of the reed switch 26 (i.e., the flux densities at which the reed switch 26 opens and closes).

The reed switch 26 responds to the magnetic flux densities by assuming either an open (non-conductive) state or closed (conductive) state. The state of the reed switch 26 is dependent upon (1) the shape and stiffness of the reeds 42, (2) the density and direction of the magnetic flux lines, (3) the hysteresis of the reeds 42 and (4) the amount of magnetic energy stored in the reeds 42. In the absence of a magnetic field, the reeds 42 are separated. Thus, the reed switch 26 is normally open. Under the influence of the magnetic field passing along the length of these reeds 42, however, a magnetic force deflects the overlapping ends of the reeds 42. As a result, the reeds 42 make contact and the reed switch 26 becomes conductive. If the reeds 42 are stiff, a greater magnetic force will be required to close the switch.

Although the state of the reed switch 26 is dependant upon the density of the magnetic flux lines, the reed switch 26 does not have to be manufactured such that it operates within a specific magnetic flux density. In the present invention, the control unit 30 adjusts the density of the magnetic flux lines provided by the bias coil 28 to accommodate the operating characteristics of the reed switch 26. Thus, the reed switch 26 does not have to be manufactured with great precision. Instead, the reed switch 26 can be any well known, standard type.

Figure 3:
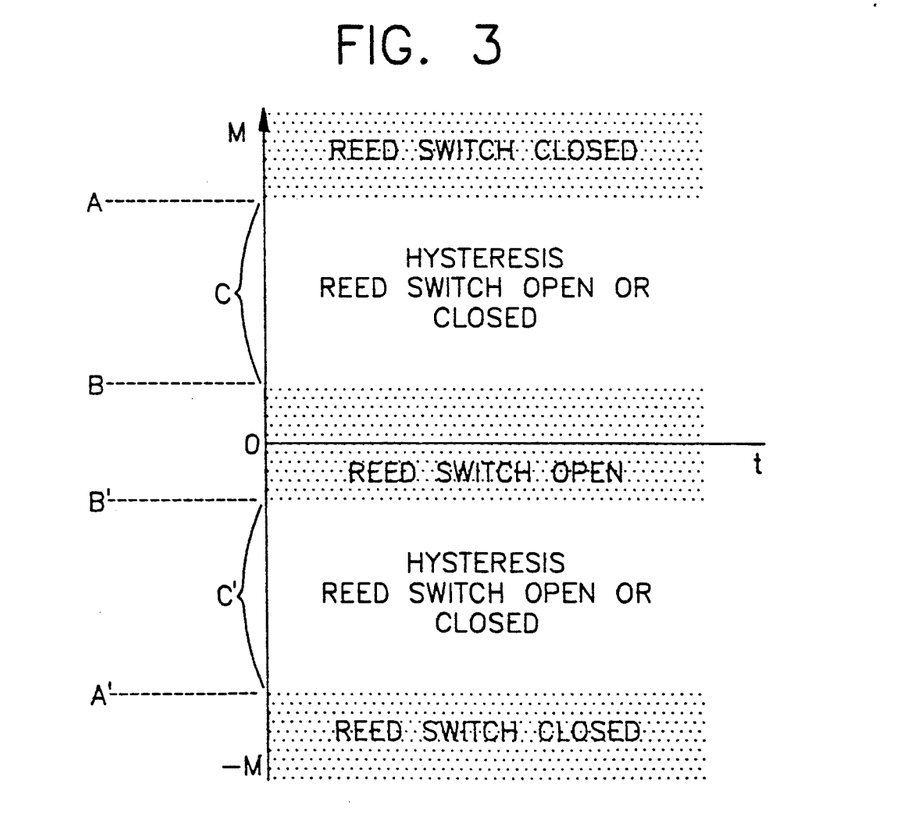
FIG. 3 is a state diagram of the reed switch illustrated in FIG. 2.

Referring now to FIG. 3, a state diagram shows the magnetic characteristics of the reed switch 26. Closing switching state transition levels A and A' indicate the magnetic flux densities above which the reed switch 26 closes, and open switching state transition levels B and B' indicate the magnetic flux densities below which the reed switch 26 opens. Between the transition levels A and B and A' and B', respectively, there is a region in which the reed switch 26 may remain either open or closed, depending upon its prior switching state. This is known as the hysteresis region C or C'. For example, if the magnetic flux density is dropped into hysteresis region C from above transition level A, in which the reed switch 26 is closed, the reed switch 26 will remain closed. Conversely, if the magnetic flux density is raised into hysteresis region C from below transition level B, in which the reed switch 26 is open, the reed switch 26 will remain open. Thus, application of a magnetic flux density in the hysteresis region C will not cause the reed switch 26 to change states.

The switching processes of the reed switch 26 are altered by the storage of magnetic energy (magnetization) of the reeds themselves. Such magnetization has a decay time of the order of seconds and either adds to or subtracts from externally applied magnetic fields. As a result, switching in the immediate regions of the open state switching transition levels B and B' may cause anomalies to appear due to recent past time variant history of magnetic fields passing through the reed switch 26.

Figure 4:
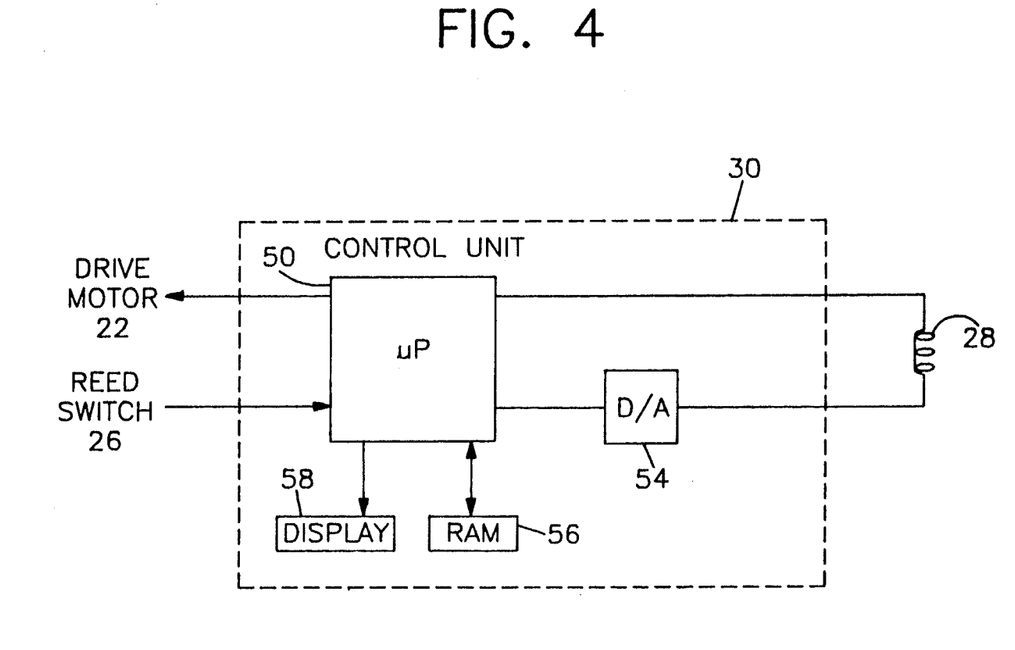
FIG. 4 is a schematic diagram of a control unit which forms a part of the system illustrated in FIG. 1.

Referring now to FIG. 4, there is shown a schematic diagram of the control unit 30. The control unit 30 includes a microprocessor 50, which controls the operation of the drive motor 22, supplies the waveform to the bias coil 28 and monitors the state of the reed switch 26. The terminals of the bias coil 28 are connected to the microprocessor 50 through a digital-to-analog (D/A) converter 54. The microprocessor 50 can thus control a ±2.5 voltage drop across the bias coil 28. The microprocessor 50 further includes random access memory (RAM) 56 and a display unit 58, which displays the time measured for the blood sample 14 to clot. Since the general principles of construction of microprocessors are well known, selection of a particular type of microprocessor is left to those skilled in the art.

It is one function of the microprocessor 50 to distinguish between the various positions of the magnet 16. This function is accomplished by energizing the bias coil 28 to produce a magnetic field having a time-varying flux density, and simultaneously monitoring transitions in the state of the reed switch 26. The microprocessor 50 commands the D/A converter 54 to energize the bias coil 28 by means of a voltage waveform. The waveform has a frequency of one hertz and comprises three phases: a first phase, which corresponds to a high-level voltage $V_H$; a second phase, which corresponds to a low-level voltage $V_L$; and an intermediate phase, which corresponds to an intermediate-level voltage $V_M$.

The high-level voltage $V_H$ of the first phase is equal to the maximum voltage deliverable by the D/A converter 54. The resulting magnetic field forces the reed switch 26 to close and store as much magnetic energy in the reeds as possible. The duration of this first phase must be adequate to assure near steady-state magnetic energy storage conditions within the reed switch 26. An exemplary duration for a one hertz frequency is 850 milliseconds. This phase is referred to as the "Gaussing" phase.

The low-level voltage $V_L$ of the second phase is lowered or reversed to force the reed switch 26 to open, even in the presence of magnet 16 in the initial position. Thus, the low-level voltage $V_L$ is selected to assure that the magnetic field of the bias coil 28, when added to that of the magnet 16 in its initial position, will always cause the reed switch 26 to open during the second phase of the waveform. The duration of the second phase is adequate to assure mechanical operation of the reed switch 26, but not so long as to permit significant degaussing of the stored magnetic energy. The duration of the second phase can be, for example, between 50 and 75 milliseconds.

Figure 5A:
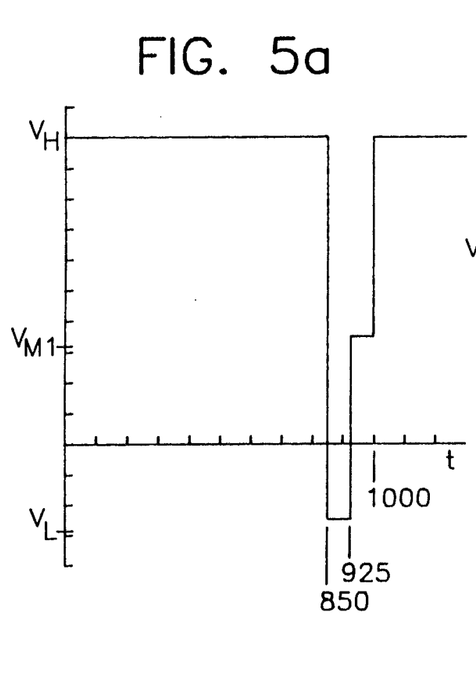
FIGS. 5a–5c are diagrams of voltage waveforms applied to the bias coil, which coil forms a part of the system illustrated in FIG. 1.
Figure 5B:
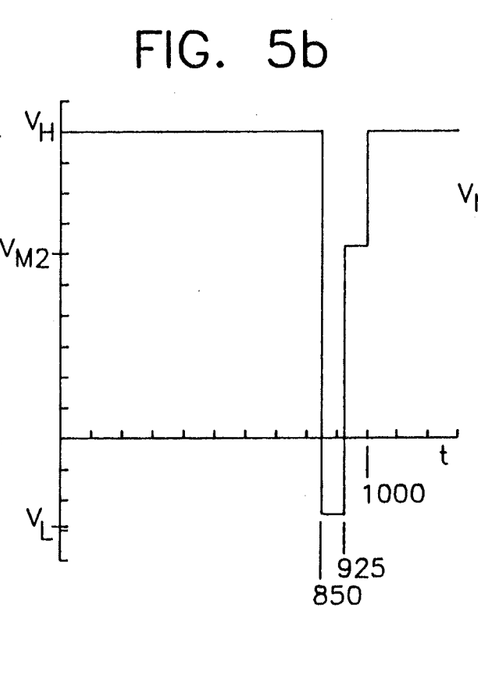
Figure 5C:
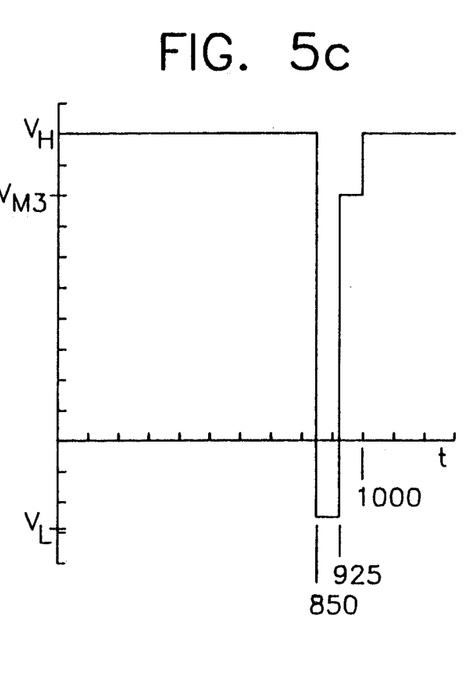
Figure 6A:
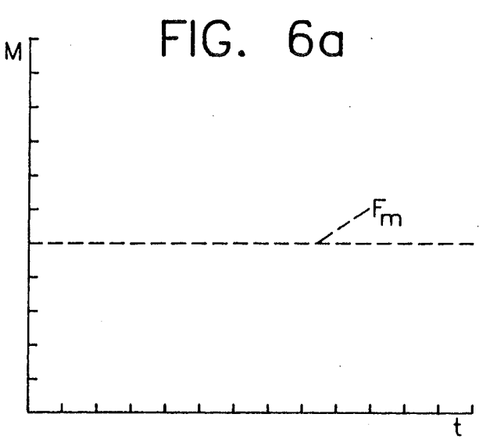
FIGS. 6a–6d are state diagrams of magnetic fields provided by the magnet at various displacements from the reed switch, the magnetic fields being observed at the reed switch.
Figure 6B:
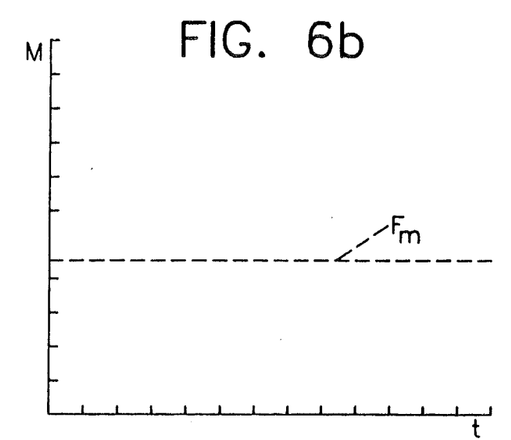
Figure 6C:
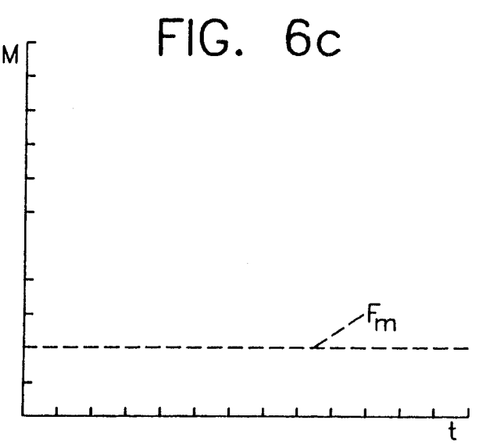
Figure 6D:
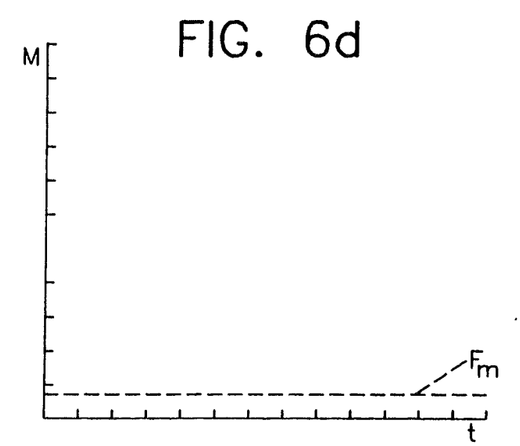

The intermediate-level voltage $V_M$ of the third phase consists of voltages that are calibrated to cause the reed switch 26 to close only when the magnet 16 is within a certain specific displacement of the reed switch 26. The duration of the third phase is adequate to assure mechanical operation of the reed switch 26 and subsequent interrogation of its switching state by the microprocessor 50. An exemplary duration can range between 50 and 75 milliseconds. There are three specified displacements of the magnet 16 from the reed switch 26; therefore, there are corresponding intermediate values for the intermediate-level voltage $V_M$: a first value $V_{M1}$, a second value $V_{M2}$ and a third value $V_{M3}$. When the intermediate-level voltage $V_M$ equals the first value $V_{M1}$, the reed switch 26 is closed whenever the magnet 16 is within ±10 degrees of the initial position. The corresponding waveform is shown in FIG. 5a. For the intermediate voltage $V_M$ equal to the second value $V_{M2}$, the reed switch 26 is closed whenever the magnet 16 is within ±90 degrees of the initial position (see FIG. 5b), and for the intermediate voltage $V_M$ equal to the third value $V_{M3}$, the reed switch 26 is closed whenever the magnet 16 is within ±180 degrees of the initial position (see FIG. 5c)

FIGS. 6a-6d illustrate the relative strength of the magnetic field $F_M$ provided by the magnet 16 and observed at the reed switch 26. The distance of the magnet 16 from the reed switch 26 affects the strength of the magnetic field $F_M$ passing through the reed switch 26. The magnetic field $F_M$ is at its strongest when the magnet 16 is at its closest, aligned position relative to the reed switch 26 (see FIG. 6a). The magnetic field $F_M$ at the reed switch 26 is somewhat reduced when the magnet 16 lies at the bottom of the test tube 12 but is cocked or not aligned (see FIG. 6b). The magnetic field $F_M$ is still further reduced when the magnet 16 "toggles" and is displaced or rotated 90 degrees from its initial position (see FIG. 6c). Finally, magnetic field $F_M$ is at its weakest when the magnet 16 is displaced by rotating a full 180 degrees within the test tube 12 (see FIG. 6d).

Referring now to FIGS. 7a-7f, there are shown superpositions of magnetic fields provided by the bias coil 28 and the magnet 16 and onto the state diagram of the reed switch 26 (FIG. 3). Each figure shows a position of the magnet 16 and a corresponding waveform during the analytic operation of the present invention.

Figure 7A:
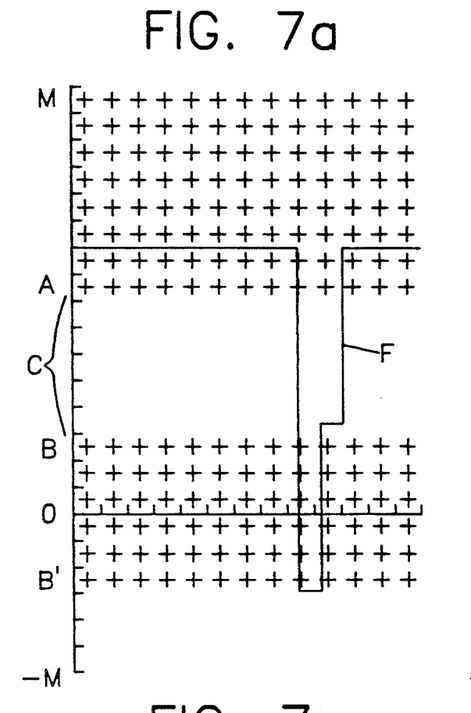
FIGS. 7a–7g are state diagrams of superimposed magnetic fields at the reed switch for various displacements of the magnet from the reed switch and for the magnetic fields provided by the bias coil.

In FIG. 7a, the switching conditions are shown for the start of the analytic operation. There is no magnet 16 in the test well 20 and the intermediate-level voltage $V_M$ being applied to the bias coil 28 equals the first value $V_{M1}$. During the first phase, the combined magnetic field F observed at the reed switch 26 exceeds that required to reach the closing switching state transition level A. Thus, the reed switch 26 is closed. Next, during the second phase, the combined magnetic field F is caused to pass through the open switching state transition level B, thereby to open the reed switch 26. In practice it is possible that the combined magnetic field may pass entirely through the open switching state zone and into the hysteresis zone C'. Should this occur, the time during which the combined magnetic field F is within the open switching state zone must be of a duration long enough to overcome mechanical/inertial processes, 50 to 75 milliseconds, for example; otherwise the switching state may remain in the closed condition. During the third phase, when voltage $V_{M1}$ is applied to the bias coil 28, the combined magnetic field F passes into the hysteresis region C. Thus, the reed switch 26 remains open.

Figure 7B:
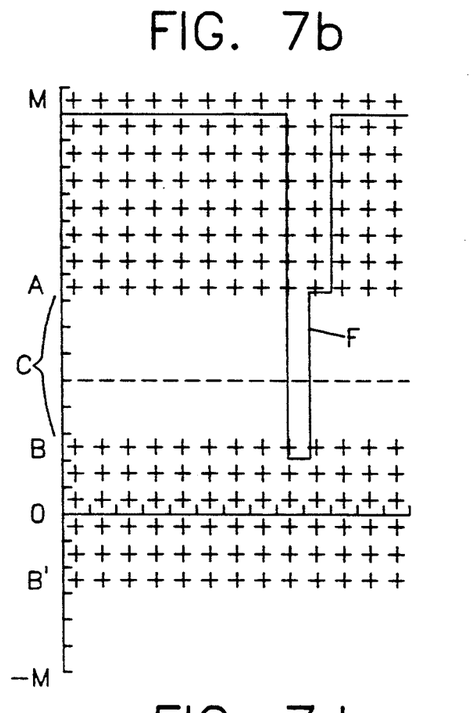

In FIG. 7b, the test tube 12 is placed in the test well 20 and the magnet 16 is located at its initial position. During the first and second phases, the states of the reed switch 26 are closed and open respectively. During the third phase, when intermediate-level voltage $V_M$ equals the first value $V_{M1}$, the combined magnetic field F of the magnet 16 and bias coil 28 exceed the closing switching state transition level A. Thus, the reed switch 26 is closed and a switching transition occurs at the third phase.

Figure 7C:
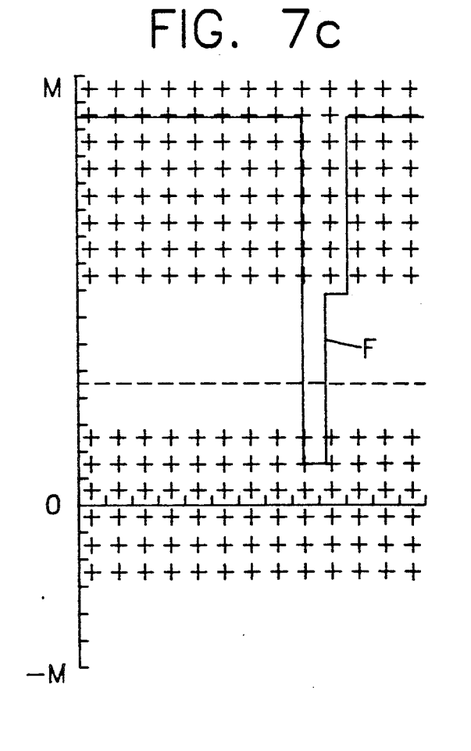

In FIG. 7c, the magnet 16 becomes unaligned with the reed switch 26. During the third phase, when intermediate-level voltage $V_M$ equals the first value $V_{M1}$, the combined magnetic field F of the magnet 16 and bias coil 28 fail to exceed the closing switching state transition level A. Thus, the reed switch 26 stays open and there is no transition.

Figure 7D:
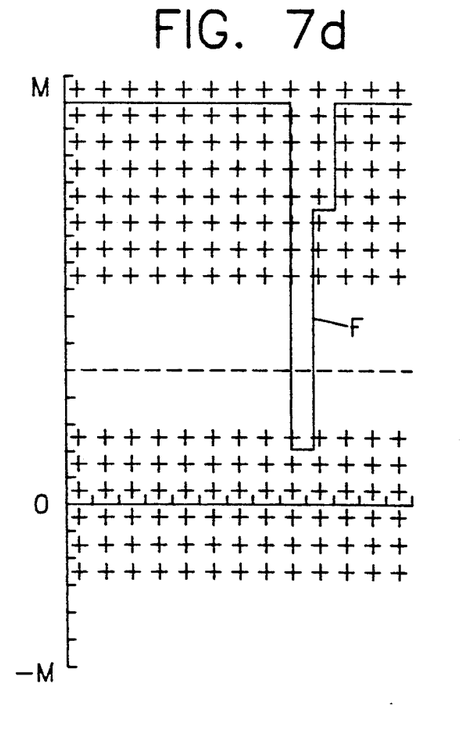

In FIG. 7d, the magnet 16 is once again in the initial position, except that the intermediate-level voltage $V_M$ equals the second value $V_{M2}$. During the first and second phases of the waveform, the switching states of reed switch 26 are closed and open, respectively. During the third phase, the switching condition is clearly above the closing switching state transition level A.

Figure 7E:
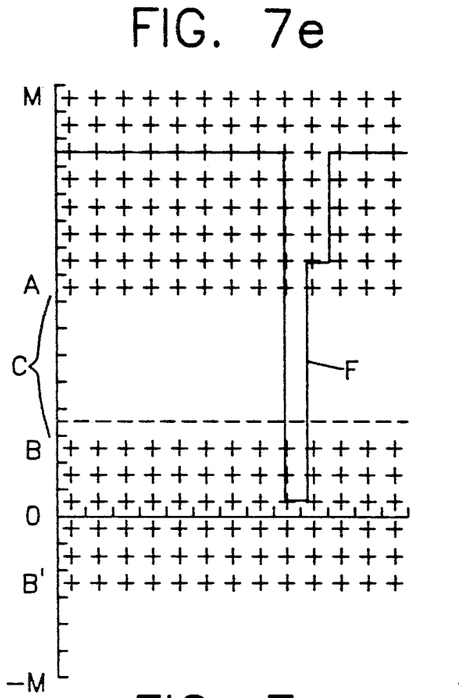

In FIG. 7e, the magnet 16 is displaced from its initial position, and the density of combined magnetic field F begins to decrease. Here, the magnet 16 has not yet been displaced from the reed switch 26 by 90 degrees, and the combined magnetic field F still exceeds the closing switching state transition level A during the third phase of the waveform. Thus, the reed switch still operates from the open state to the closed state during the second and third phases, respectively.

Figure 7F:
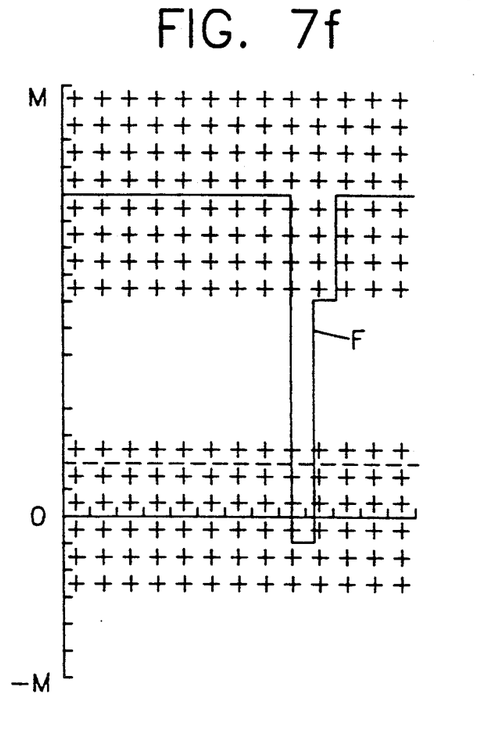

In FIG. 7f, however, the magnet 16 is displaced by 90 degrees 26. Because these combined magnetic field F fails to exceed the closing switching state transition level A during the third phase, when the intermediate-level voltage $V_M$ equals the second value $V_{M2}$, the reed switch 26 fails to make the transition from an open state to a closed state. The microprocessor 50 interprets this condition to indicate an end point, provided that it is confirmed through several waveform cycles.

Figure 7G:
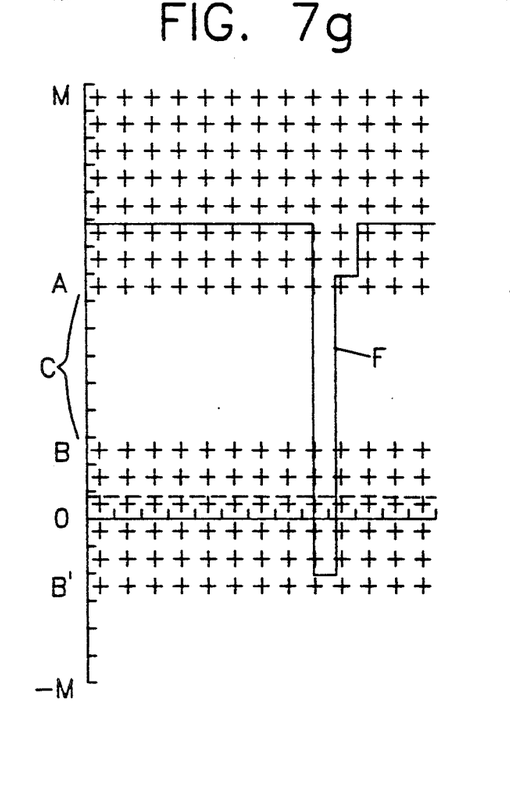

In FIG. 7g, the final validation of the analytic operation is shown. The intermediate-level voltage $V_M$ applied to the bias coil 28 equals the third value $V_{M3}$. If the magnet 16 is located somewhere in the test well 20, the combined magnetic field F will exceed the closing switching level transition state A and the reed switch 26 will close during the third phase. The microprocessor 50 will indicate that the analytic operation was successful and will accept the observed end point condition as having been caused by rotational displacement of the magnet 16. If, however, the reed switch 26 does not close during the third phase, the microprocessor 50 indicates that the analytic operation was aborted and that the test was terminated by removal of the test tube 12 from the test well 20.

To execute the analytic operation, an operator injects a sample of blood 14 into the test tube 12 and inserts the test tube 12 into the test tube well 20 of the analyzer Then, he commands the microprocessor 50 to execute a resident program for the analytic mode. The microprocessor 50 determines automatically the time required for the blood 14 sample to coagulate.

Figure 8A:
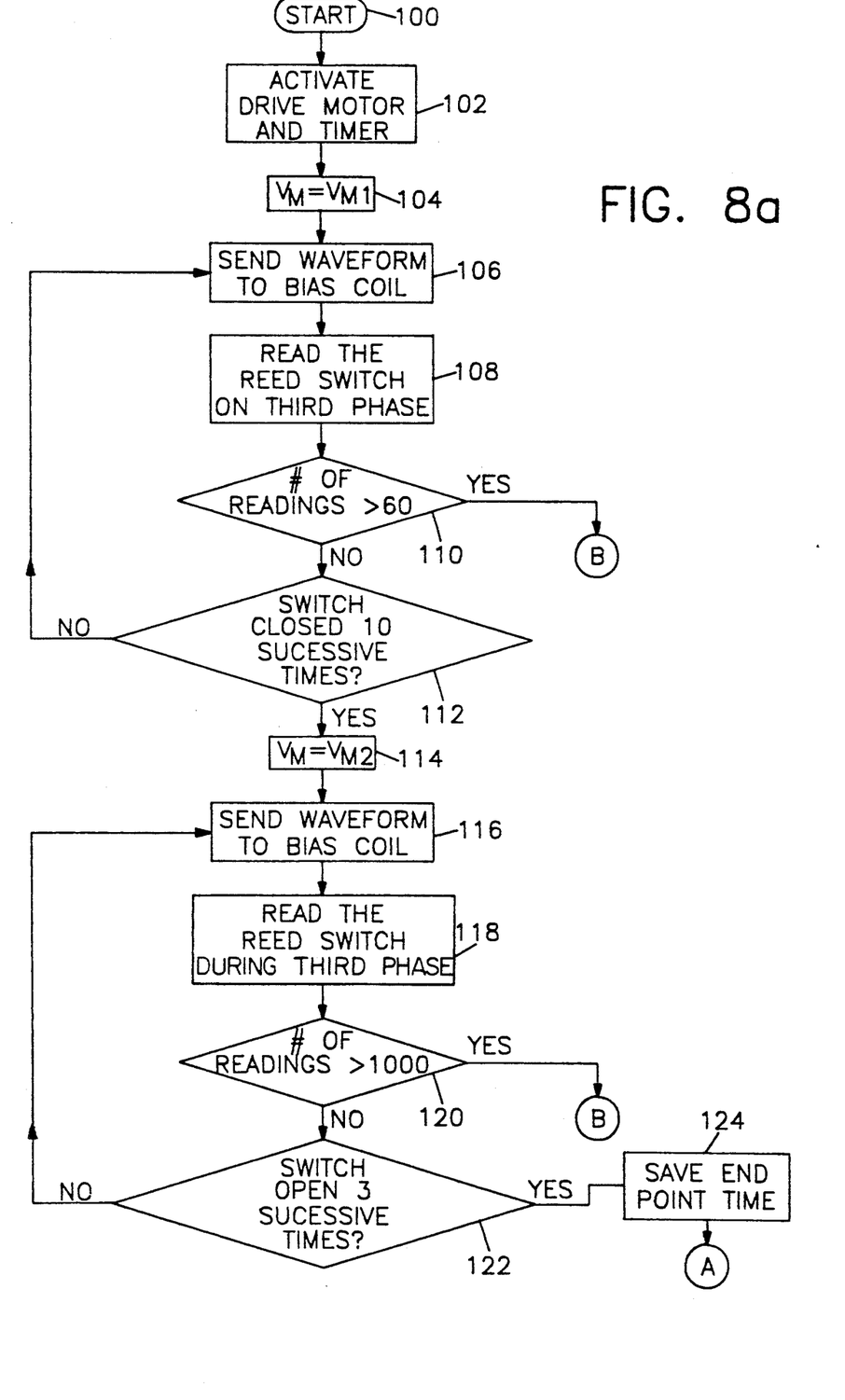
FIGS. 8a and 8b are a flow chart of a microprocessor program for the analytic mode.
Figure 8B:
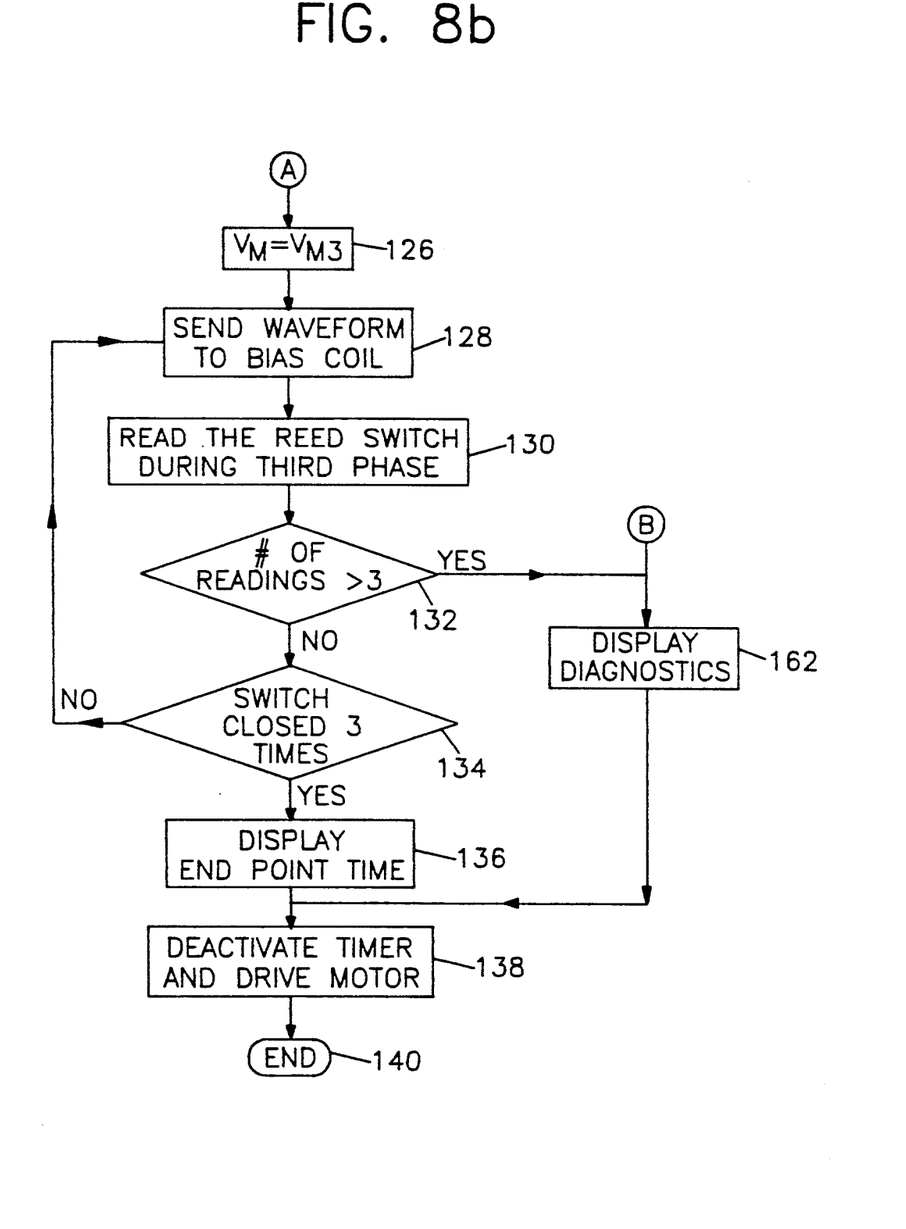

Referring now to FIGS. 8a and 8b, there is shown a flow chart of the microprocessor-resident program that implements the analytic mode. The microprocessor 50 starts the program (module 100), actuates the test tube drive motor 22 and initiates a timer (module 102) and then sets the intermediate-level voltage $V_M$ of the waveform to the first value $V_{M1}$ (module 104). Then, the microprocessor commands the D/A converter 54 to supply the waveform to the bias coil 28 at a frequency of one hertz (module 106).

During the first phase of the waveform, the magnetic field produced by the bias coil 28 forces the reed switch 26 to a closed state regardless of the orientation or presence of magnet 16. Immediately thereafter, during the second phase of the waveform, the magnetic field provided by the bias coil 28 causes reed switch 26 to open, again regardless of the orientation or presence of magnet 16. During the third phase of the waveform, the magnetic fields provided by both the magnet 16 and bias coil 28 cooperate to close the reed switch 26 if and only if the magnet 16 is at its lowermost, aligned, initial position.

The microprocessor 50 reads the state of the reed switch 26 once during the third phase of the waveform (module 108). If the reed switch 26 is not in a closed state ten successive times (module 112) within 60 readings (module 110), the microprocessor 50 displays diagnostic data (module 162) and terminates the test. If, however, the microprocessor 50 confirms that the magnet 16 has remained in a closed state (i.e., in the initial position) during the third phase of ten successive waveform cycles (module 112), it proceeds to the next step (module 114).

The microprocessor then sets the intermediate-level voltage $V_M$ of the waveform to the second value $V_{M2}$ (module 114) and commands the D/A converter 54 to provide the waveform to the bias coil 28 (module 116). As the waveform is being supplied to the bias coil 28 at a frequency of one hertz, the microprocessor 50 monitors the switching state of the reed switch 26 during the third phase of each waveform (module 118). If the reed switch 26 does not open for three successive cycles during the next 1000 cycles (module 120 and 122), the microprocessor 50 displays diagnostic data (module 112) and terminates the test. An analytic testing end point is defined when the microprocessor 50 detects and confirms for three successive out of 1,000 cycles that the reed switch 26 has failed to close (i.e., failed to make the transition from opened state to closed state) during the third phase of the waveform (modules 120 and 122). Such condition is caused by displacement of the magnet 16 by more than 90 degrees, indicative of the clotting of blood sample 14. The microprocessor 50 then records the time at which the reed switch 26 first failed to close and stores this time as the end point time (module 124).

Thereafter, the microprocessor 50 sets the intermediate-level voltage $V_M$ of the third phase of the waveform to the third value $V_{M3}$ (module 126), and supplies the waveform to the bias coil 28 at a frequency of one hertz (module 128). The microprocessor 50 continues to monitor the switching state of the reed switch 26 (module 130) for three waveform cycles (module 132) to verify that the reed switch closes during each third phase (module 134). If such condition is verified, the microprocessor 50 instructs the display 58 to display the previously stored end point time (module 136). Thus displayed is the time measured for the blood sample 14 to coagulate. Failure to confirm the condition is interpreted to mean that the test tube 12 and magnet 16 were withdrawn from the test well before blood 14 had a change to clot. In the event of a failure the microprocessor 50 instructs the display 58 to display a testing error message (module 162) and terminates the test. Microprocessor 50 deactivates the timer and drive motor (module 138) and ends the test (module 140).

Before running an analytic operation, the waveform must be calibrated. The magnetic field provided by the bias coil 28 is calibrated by running the analyzer 18 through n=4 positions. At each position, the magnet 16 is displaced from the reed switch 26 by a predetermined angle. Exemplary angles for the four positions are zero degrees, ten degrees, ninety degrees and one-hundred eighty degrees, respectively. To obtain the proper displacements, the operator tilts the analyzer 18, whereupon the magnet 16 remains at the bottom of the test tube 12, and the position of the reed switch 26 is displaced by the angle of tilt. In place of an analyzer 18 that is adapted to tilt, a test tube 12 having a magnet 16 affixed to one wall can be employed. An operator would manually rotate the test tube 12 and magnet 16 by the required angular displacement. The microprocessor 50 contains a memory-resident program that determines the operating characteristics of the reed switch 26 and, accordingly, determines the high-level, low-level and intermediate-level voltages $V_H$, $V_L$ and $V_M$ in order to adjust the magnetic flux density to open and close the reed switch 26. With its bias coil 28 having an adjustable flux density, the present invention can utilize reed switches having a wide range of operating characteristics.

Figure 9A:
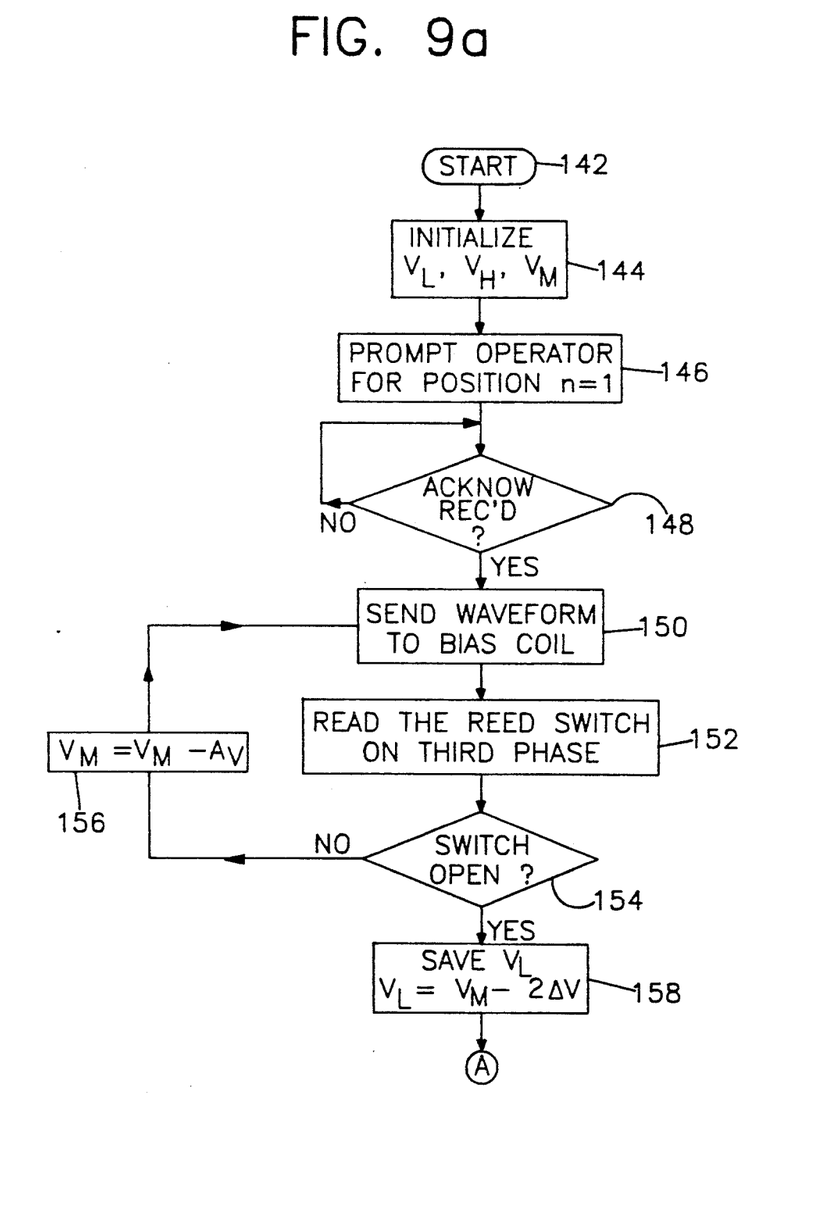
FIGS. 9a and 9b are a flow chart of a microprocessor program for the calibration mode.
Figure 9B:
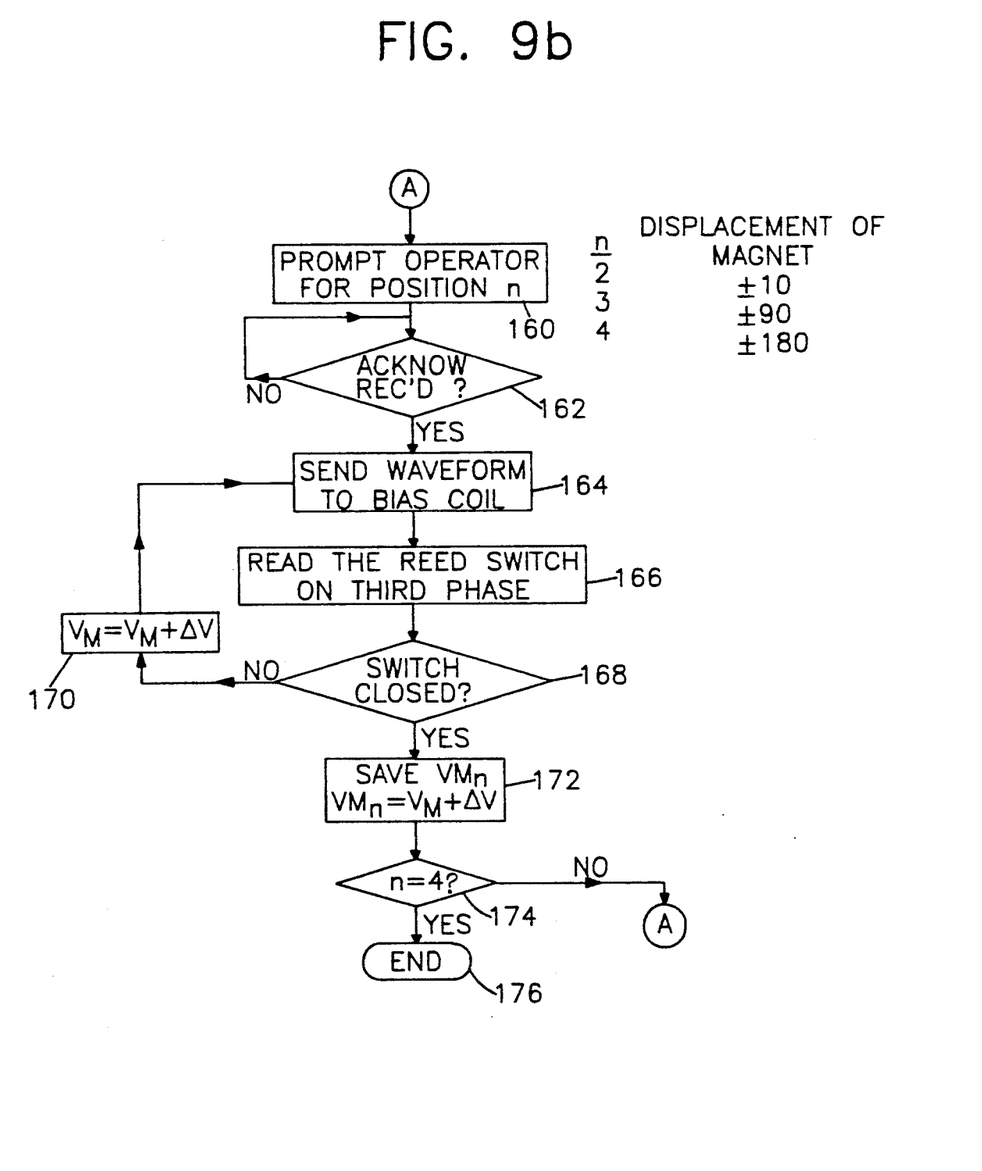

Referring now to FIGS. 9a and 9b, there is shown a flow chart of the microprocessor-resident program that implements the calibration mode. During the calibration mode, the microprocessor 50 must vary the intermediate-level voltage $V_M$ until the reed switch 26 closes. The microprocessor 50 commands the D/A converter 54 to increase or decrease the intermediate-level voltage $V_M$ by an incremental voltage $\Delta V$. This incremental voltage $\Delta V$ is a function of the resolution of the D/A converter 54.

The microprocessor 50 starts the program (module 142) and initializes the high-level, low-level and intermediate-level voltages $V_H$, $V_L$ and $V_M$ at a value equal to half the voltage supply (module 144). Then, it determines the low-level voltage $V_L$ required to open the reed switch 26 during the second phase of the waveform. The microprocessor 50 prompts the operator to set up the analyzer 18 in the first position, in which the magnet is displaced from the reed switch 26 by zero degrees (module 146). The microprocessor 50 waits until it receives an acknowledgement from the operator that the analyzer 18 is set up (module 148), and then commands the D/A converter 54 to send a waveform to the bias coil 28 (module 150). During the third phase of the waveform, the microprocessor 50 reads the state of the reed switch 26 (module 152). If the reed switch 26 is not open (module 154), the microprocessor 50 decreases the intermediate-level voltage $V_M$ by the incremental voltage $\Delta V$ (module 156) and sends another waveform (module 150). The microprocessor 50 repeats these steps until the reed switch 26 opens. Once the reed switch 26 opens, the microprocessor 50 stores the resultant intermediate-level voltage $V_M$ in microprocessor RAM 56 as the low-level voltage $V_L$ (module 158). If the reeds 42 are not stiff, such that the magnet 18 alone causes the reed switch 18 to close, the current must be reversed. Thus, the reed switch 26 opens during the second phase of the waveform, regardless of the displacement of the magnet 16 from the reed switch 26.

After determining the low-level voltage $V_L$, the microprocessor 50 determines the first, second and third values $V_{M1}$, $V_{M2}$ and $V_{M3}$ of the intermediate-level voltage $V_M$. The microprocessor 50 prompts the operator to set up the analyzer 18 (module 160) in the second position, which corresponds to the maximum angular displacement of the magnet 16 for which the reed switch 26 remains closed during the test tube insertion or initiating phase of analytic operation. An exemplary displacement is ten degrees. After the microprocessor an acknowledgement from the operator (module 163), it commands the D/A converter 54 to send the waveform to the bias coil 28 (module 164). During the third phase of the waveform, the microprocessor 50 reads the state of the reed switch 26 (module 166). If the reed switch 26 is open (module 168), the microprocessor 50 increase the intermediate voltage $V_M$ by the incremental voltage $\Delta V$ (module 170) and sends another waveform to the bias coil 28 (module 164). These steps are repeated until the reed switch 26 closes. Once the reed switch closes, the microprocessor 50 stores in microprocessor RAM 56 the current value $V_{M1}$ as the intermediate voltage $V_{M1}$ (module 172). Thus, the reed switch 26 stays closed during the third phase of this waveform, provided that the magnet 16 is displaced no more than 10 degrees from the reed switch 26.

The microprocessor 50 repeats this sequence (modules 160–172) for the third position, in which the magnet is displaced from the reed switch by ninety degrees, and for the fourth position, in which the magnet 16 is displaced from the reed switch by one-hundred eighty degrees. The final value $V_{M2}$ of the intermediate-level voltage $V_M$ ensures that the reed switch 26 stays closed during the third phase of the waveform, provided that the magnet 16 is displaced no more than 90 degrees from the reed switch 26. The third value $V_{M3}$ of the intermediate voltage $V_M$, which is determined during the fourth position, ensures that the reed switch 26 is closed during the third phase of this waveform, regardless of where the magnet 16 is displaced from reed switch 26. When all four positions have been performed (module 174), the microprocessor 50 ends the calibration program (module 176).

The present invention uses only the closing switching state transition level A to determine the time required for blood to clot. Thus, it avoids dependence upon the natural hysteresis C and opening switching state transition level B characteristics of reed switches, as required by the prior art systems, and circumvents the previously described problems in using reed switches as magnetic field sensors.

Further, the present invention seeks to make constant the magnetic energy stored in the reed switch 26 by applying a maximum available magnetic field to the reed switch 26 for as much as the waveform cycle as available, allowing for mechanical time requirements of the second and third waveform phases. An advantage to applying such field is that the magnetic energy stored in the reed switch 26 is essentially maximized throughout the waveform cycle. Thus, the undesirable, time-dependent effects caused by magnetic storage are reduced, and previously observed problems with non-responsive reed switches due to "sticking" reeds in the vicinity of the switching state transitions (FIG. 3) are effectively eliminated.

Finally, the present invention synthesizes the operating characteristics of the reed switch 26 and uses these characteristics to adjust the magnetic field provided by the bias coil 28. Thus, the magnetic field of the bias coil 28 can be adjusted to cause the reed switch 26 to open and close, regardless of the operating characteristics of the reed switch 26. As a result, reed switches 26 having a wide range of operating characteristics can be employed by the present invention. This is especially important when lower quality reed switches are employed.

It will be understood that the embodiment described herein is merely exemplary and that a person skilled in the art may make many variations and modifications without departing from the spirit and scope of the invention. All such modifications are intended to be included within the scope of the invention as defined in the appended claims.

What is claimed is:

1. A system for detecting the coagulation of blood from a liquid to a clot comprising:
    adjustable-variable source means for providing magnetic flux lines having a density that varies in a time repetitive sequence and that is adjustable;
    switching means, magnetically coupled to said adjustable-variable source means by said flux lines, for switching from a second state to a first state when said density of said flux lines enters a first density region;
    determining means, responsive to said switching means, for determining said first density region; and
    adjusting means, responsive to said determining means and operative on said adjustable-variable source means, for adjusting said density of said flux lines at a first level such that said variation causes said density of said flux lines to fall outside of said first density region, whereby non-coagulation of blood causes said switching means to switch from said second state to said first state or whereby said coagulation of blood causes said switching means not to switch from said second state.

2. A system according to claim 1, wherein said switching means switches to said second state when said density of said flux lines enters a second region, and wherein a hysteresis region is located between said first and second density regions.

3. A system according to claim 2, wherein said switching means includes a reed switch.

4. A system according to claim 3, wherein said determining means further determines said second density region of said reed switch, and wherein said adjusting means includes first setting means for setting said density of said flux lines in said second region.

5. A system according to claim 4, further including detecting means, responsive to said switching means, for detecting when said reed switch switches from said second state to said first state.

6. A system according to claim 5, further including measuring means, responsive to said detecting means, for measuring the time for blood coagulation.

7. A system according to claim 6, wherein said magnetic flux lines consists of first and second lines of flux, and wherein said adjustable-variable source means includes:
    a first source, located in proximity of said reed switch, for providing said first lines of flux;
    a second source for providing said second lines of flux; and
    actuatable moving means for moving said second source from a first position, in which said second source is in proximity of said reed switch, to a second position, such that said density of said flux lines magnetically coupled to said reed switch is decreased, said moving means being actuated when said blood clots.

8. A system according to claim 7, wherein said second source is a permanent magnet.

9. A system according to claim 7, wherein said first source is an electromagnetic coil, wrapped around said reed switch, and wherein said system further includes waveform means for sending a waveform comprising said time repetitive sequence to said electromagnetic coil, said waveform having a low-level voltage, controlled by said first setting means to cause said density of said magnetic flux lines to enter said second density region, said waveform having an intermediate-level voltage, controlled by said second setting means to cause said density of said magnetic flux lines to be at said first level, and wherein said detecting means detects said state of said switch while said intermediate-level voltage is applied to said electromagnetic coil.

10. A system according to claim 9, wherein said waveform also has a high-level voltage, wherein said adjustable means includes third setting means for setting said high-level voltage such that said density of said magnetic flux lines is in said first density region.

11. A system according to claim 10, wherein said duration of said waveform is one second, wherein said third setting means provides said high-level voltage for 850 milliseconds, wherein said first setting means provides said low-level voltage for 75 milliseconds, and wherein said second setting means provides said intermediate-level voltage for 75 milliseconds.

12. A system according to claim 11, wherein said waveform is sent to said electromagnetic coil at a frequency of one hertz.

13. A system according to claim 12, wherein said waveform means is a digital to analog converter.

14. A system according to claim 1, wherein a microprocessor comprises said adjusting means, said determining means, said detecting means and said measuring means.

15. A system according to claim 7, wherein said actuatable moving means includes:
a test tube containing said blood, said second source being immersed in said blood; and
rotating means for rotating said test tube, whereby there is a relative rotational motion between said test tube and said second source when said blood is unclotted, and whereby said clotted blood causes said second source to move conjointly with said test tube from its said first position to its said second position.

16. A system for detecting the coagulation of blood from a liquid to a clot comprising:
a vessel containing said blood;
adjustable magnetic field means, located external said vessel, for providing an adjustable magnetic field;
permanent magnetic field means, disposed within said vessel, for providing a permanent magnetic field, which combines with said adjustable magnetic field to provide a combined magnetic field, whereby said combined magnetic field is adjusted by adjusting said adjustable magnetic field means;
switching means, magnetically coupled to said permanent magnetic field means and said adjustable magnetic field means by said combined magnetic field, for switching from a second state to a first state when said density of said combined magnetic field enters a first density region;
moving means for providing relative motion between said vessel and said permanent magnetic field means until said blood clots, whereupon said permanent magnetic field means moves with said vessel such that the density of said combined magnetic field varies in a time repetitive sequence;
determining means, responsive to said switching means, for determining said first density region; and
adjusting means, responsive to said determining means and operative on said adjustable magnetic field means, for adjusting said density of said adjustable magnetic field such that said variation causes said density of said combined magnetic field to fall outside of said first density region, whereby non-coagulation of blood causes said switching means to switch from said second state to said first state or whereby said coagulation of blood causes said switching means not to switch from said second state.

17. A method of detecting the coagulation of a sample of blood from a liquid to a clot in a system including a vessel containing said blood, adjustable magnetic field means, located external said vessel, for providing an adjustable magnetic field; a ferromagnetic member, disposed within said vessel, for providing a permanent magnetic field, and a normally-open reed switch, magnetically coupled to said adjustable magnetic field means by said adjustable magnetic field, said method comprising the steps of:
(a) adjusting said adjustable magnetic field to a first level at which said reed switch closes;
(b) placing said ferromagnetic member in proximity of reed switch;
(c) adjusting the adjustable magnetic field to a second level at which the reed switch opens;
(d) rotating said vessel to create a relative rotational motion between said ferromagnetic member and said vessel;
(e) adjusting the adjustable magnetic field to a third level; and
(f) monitoring the state of said reed switch whereupon if said blood has coagulated the reed switch remains open.

18. A method according to claim 17, further comprising the steps of:
(e1) adjusting the density of said adjustable magnetic field to close said reed switch; and
(e2) adjusting the density of said adjustable magnetic field to allow said reed switch to open, wherein said steps (e1) and (e2) are performed prior to performing step (e), and wherein said steps (e1), (e2), (e) and (f) are repeated.

19. A method according to claim 18, wherein steps (e1), (e2) (e) and (f) are repeated at a one hertz rate.

20. A method according to claim 19, wherein said reed switch is closed for 850 milliseconds during step (e1) and opened for 75 during step (e2), and wherein said adjustable magnetic field is applied at said first level for 75 milliseconds during step (e).

* * * * *